United States Patent [19]

Leckrone et al.

[11] 4,432,362
[45] Feb. 21, 1984

[54] ATRIAL-BASED, ATRIAL-VENTRICULAR SEQUENTIAL CARDIAC PACER

[75] Inventors: Michael E. Leckrone, Indianapolis, Ind.; James P. Martucci, Miami, Fla.

[73] Assignee: Cordis Corporation, Miami, Fla.

[21] Appl. No.: 355,367

[22] Filed: Mar. 8, 1982

Related U.S. Application Data

[62] Division of Ser. No. 153,422, May 27, 1980, Pat. No. 4,386,610.

[51] Int. Cl.³ .............................................. A61N 1/36
[52] U.S. Cl. .............................................. 128/419 PG
[58] Field of Search .............................. 128/419 PG

[56] References Cited

U.S. PATENT DOCUMENTS

| | | | |
|---|---|---|---|
| 3,677,251 | 7/1972 | Bowers | 128/419 PG |
| 3,747,604 | 7/1973 | Berkovits | 128/419 PG |
| 3,783,878 | 1/1974 | Thaler et al. | 128/419 PG |

OTHER PUBLICATIONS

Funke, "Die Optimierte Sequentielle Stimulation . . . ", Herz/Kreisl 10, Nr. 10 (1978), pp. 479–483.

*Primary Examiner*—William E. Kamm
*Attorney, Agent, or Firm*—Kenway & Jenney

[57] ABSTRACT

Atrial refractory and ventricular inhibit functions are independently implemented in an atrial-synchronized pacer. Spontaneous signals on the ventricular lead inhibit ventricular stimulation for a predetermined interval independent of the atria, except when there is noise on the ventricular lead. The atrial-based pacing logic establishes the usual refractory period following spontaneous P-waves, and when noise is detected on the atrial lead, the pacing logic reverts to a fixed atrial rate. The ventricular-inhibited logic includes a retriggerable noise timing circuit and a non-retriggerable inhibit timing circuit both triggered by the output of the ventricular sense amplifier. The output of the inhibit circuit disables the ventricular stimulation output circuit. However, if the output of the noise circuit stays high for an interval indicative of electromagnetic interference, the trigger input to the inhibit timing circuit is disabled to permit ventricular stimulation. Meanwhile, the pacing logic institutes fixed rate pacing due to atrial noise. In AV synchronous and atrial-synchronized AV sequential pacer embodiments, the digital pacing logic uses existing circuitry while the ventricular-inhibited logic is implemented by an add-on RC-timed circuit. In the AV sequential pacer, the AV delay circuit is separate from the pacing logic, and its input is provided by the atrial sense amplifier normally and by the output of the pacing logic during ventricular noise.

13 Claims, 10 Drawing Figures

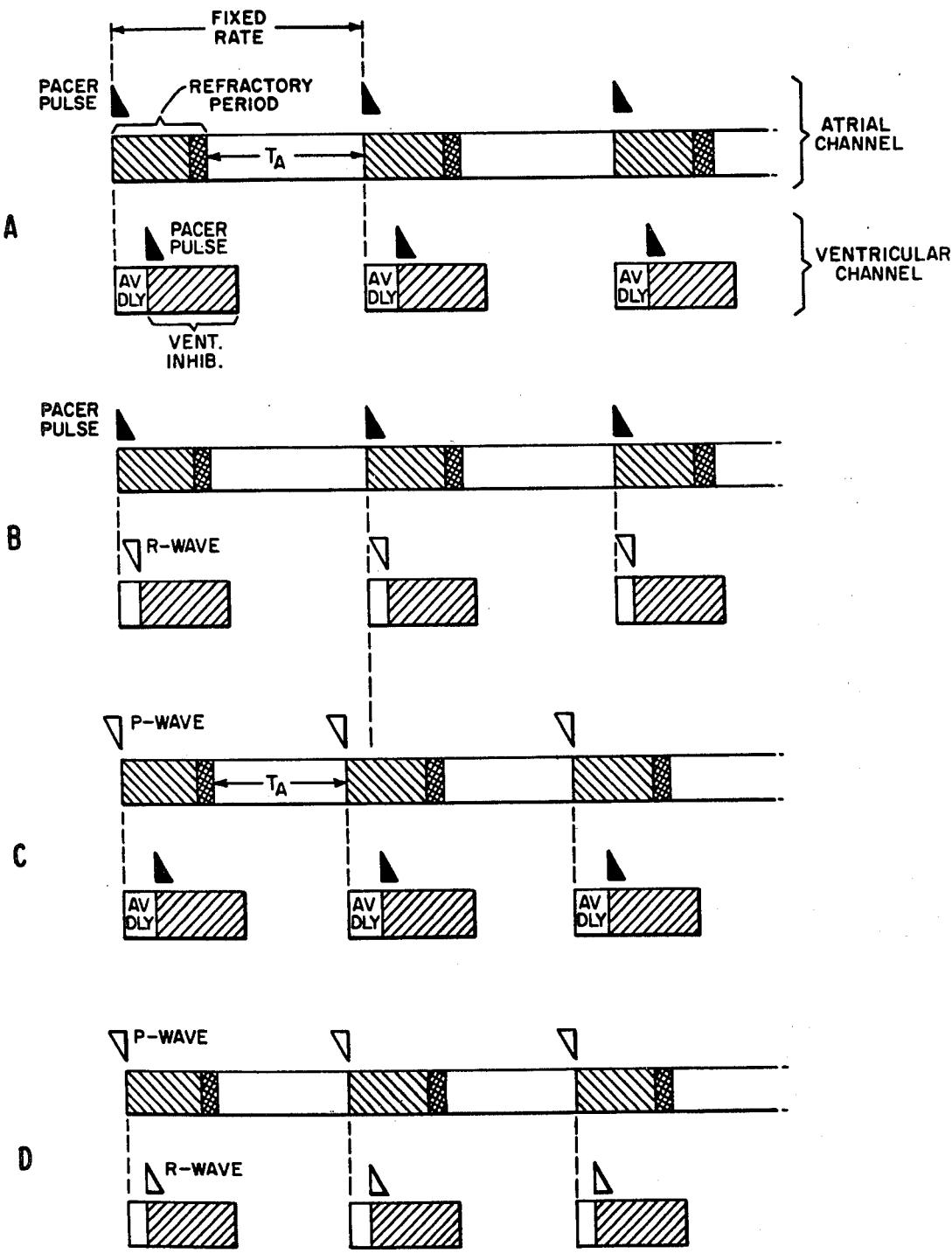

ATRIAL-BASED, ATRIAL-VENTRICULAR SEQUENTIAL CARDIAC PACER

CROSS REFERENCE TO RELATED APPLICATIONS

This application is a division of Ser. No. 153,442, filed May 27, 1980, now U.S. Pat. No. 4,386,610 by Micheal E. Leckrone entitled "Ventricular-Inhibited Cardiac Pacer."

BACKGROUND OF THE INVENTION

The invention relates generally to cardiac pacers, and more particularly to cardiac pacing systems having means for avoiding competition with spontaneous depolarization.

The physical characteristics of the human heart lend themselves to various interactive artificial pacing systems. There are two major pumping chambers in the heart, the left and right ventricles. Simultaneously contracting, these chambers expel blood into the aorta and the pulmonary artery. Blood enters the ventricles from the left and right atria, respectively. The atria are smaller antechambers which contract in a separate action that precedes the major ventricular contraction by an interval of about 100 milliseconds (ms), known as the AV delay, approximately one-eighth of the cardiac cycle. The contractions arise from a wave of electrical excitation which begins in the right atrium and spreads to the left atrium. The excitation then enters the atrioventricular (AV) node which delays its passage via the bundle of His into the ventricles.

Electrical signals corresponding to the contractions appear in the electrocardiagram. A small signal known as the P-wave accompanies atrial contraction while a much larger signal, known as the QRS complex, with a normally predominant R-wave, accompanies the ventricular contraction. Repolarization prior to the next contraction is marked by another small signal in the electrocardiagram known as the T-wave. The P and R-waves can be very reliably detected as timing signals by electrical leads in contact with the respective heart chambers. The typical implanted cardiac pacer operates by supplying missing stimulation pulses on a pacing lead attached to the right ventricle. The R-wave can be sensed by the same lead. An additional lead contacts the left atrium to sense P-waves, if desired.

One of the problems treated by cardiac pacers is heart block caused by impairment of the ability of the bundle of His to conduct normal excitation from the atrium to the ventricle. It has long been apparent that in treating this form of heart disease, it is desirable to base the stimulation of the ventricles on the umimpaired P-wave cycle. This synchronization maintains the heart's normal physiological pacing pattern. Thus, the sino-atrial node, which governs the interval between atrial depolarizations (i.e., the atrial rate) according to the body's needs, controls the artificial ventricular rate in the normal manner.

It is also well known that ventricular stimulation should not be applied during the repolarization period following ventricular contraction. This period begins with the QRS complex and lasts through the T-wave (Q-T period), approximately 300 ms or three-eighths of the cardiac cycle. Stimulation during the Q-T transition can induce undesirable heart rhythms. A spontaneous ventricular beat can arise through normal AV conduction or spuriously as in ectopic ventricular activity. In the latter case, the ventricular beat does not have the normal relationship to atrial excitation.

In an asynchronous (fixed rate) pacer, it is possible that stimulation pulses will be applied to the Q-T period following a spontaneous ventricular beat, whether normally or abnormally conducted. When this happens, stimulation pulses are said to be competing with the natural activity of the heart.

In P-wave synchronized pacers, such as the "Omni-Atricor" manufactured by Cordis Corporation, the assignee of the present application, the normally conducted beat occurs simultaneously with ventricular stimulation in a noncompetitive fashion. Nevertheless, P-wave synchronized ventricular stimulation can compete with ectopic ventricular activity.

Systems for inhibiting the output of an AV synchronous pacer due to spontaneous ventricular signals have been proposed. U.S. Pat. No. 3,903,897 includes means for sensing activity on the ventricular lead and producing a Q-T logic output to a gate which controls the application of stimulation pulses to the ventricular lead. One of the problems of ventricular sensing is that noise appearing on the ventricular lead may falsely inhibit stimulation. The consequences of omitting needed stimulation can outweigh the consequences of competitive pacing. U.S. Pat. No. 3,648,707 describes a notch filter in the ventricular sensing circuitry which apparently excludes 60 Hertz signals. Unfortunately, noise is not confined to 60 Hertz but is present in our environment in varying degrees throughout the electromagnetic spectrum. In addition to the ubiquitous 60 Hertz noise, auto ignitions and hair dryers, for example, produce strong local electromagnetic interference with pulse repetition frequencies as low as 50 Hertz.

Patients without normal atrial activity, as in symptomatic bradycardia, have a need for atrial stimulation as well as ventricular stimulation which alone achieves about 75% of the combined volume flow. So-called bifocal pacers have been proposed for stimulating the atria and the ventricles, for example, in U.S. Pat. Nos. 3,747,604 and 3,783,878. While these systems are apparently capable of stimulating both chambers of the heart, they are based on ventricular timing; that is, unlike physiological pacing, the sensing of ventricular activity resets the timing mechanism.

For a pacer manufacturer, one of the rarely achieved goals in pacer development is to employ without modification circuitry which has been tested and used before for other pacers manufactured by the same company. To ensure reliability, components are usually tested and evaluated over a lengthy product qualification period, and to the extent that a new design incorporates existing circuitry its reliability for life-supporting cardiac pacers can be more accurately estimated in advance.

SUMMARY OF THE INVENTION

Accordingly, the general purpose of the invention is to inhibit ventricular stimulation during the Q-T period following a noise-free spontaneous ventricular contraction signal in a P-wave synchronized pacer. A related objective is to provide improved atrial-synchronized AV synchronous and AV sequential pacing, utilizing existing circuitry.

These and other objects of the invention are accomplished by independently implementing the atrial refractory and ventricular inhibit function in an atrial-based pacing system. Ventricular stimulation pulses are disabled following the sensing of spontaneous ventricular activity except in the presence of noise on the ventricular lead. The ventricular inhibit period is independent of the atria which synchronize the pacing mode.

In the preferred embodiment, the ventricular-inhibited logic includes a retriggerable 20 ms noise timing circuit and a non-retriggerable 280 ms inhibition timing circuit, both of which are triggered by the output of the ventricular sense amplifier. The output of the 280 ms inhibit circuit clamps the ventricular output circuit to prevent the passing of stimulation pulses to the electrode. If the output of the 20 ms noise circuit stays high for an interval indicative of noise above 50 Hertz, the trigger input to the inhibit circuit is disabled to permit ventricular stimulation pulses. Meanwhile, the atrial-synchronized pacing logic also senses noise on the atrial lead and institutes fixed rate pacing.

Two atrial-synchronized pacing systems are disclosed for use with the ventricular-inhibited logic: AV synchronous and AV sequential. In both, the pacing logic is preferably implemented from the existing digital circuitry, and the ventricular-inhibited logic package is implemented by an add-on RC-timed circuit.

The novel atrial-synchronized AV sequential pacer includes a demand pacer for the atrial channel and means for atrial triggering of an AV delay for the ventricular channel. The AV delay is preferably timed separately from the fixed atrial rate interval. The input to the AV delay circuit is provided by the atrial sense amplifier normally and by the output of the atrial pacing logic during ventricular noise. The noise output of the ventricular-inhibited logic package is used to switch the input to the AV delay circuit. The inhibit output of the ventricular-inhibited logic package gates the input to the AV delay circuit so that the earliest point at which the pacer can begin an AV delay following detection of a spontaneous R-wave is the end of the 280 ms inhibit period.

BRIEF DESCRIPTION OF THE DRAWINGS

FIG. 10 is a timing diagram showing four different modes of operation (A, B, C, D) of the AV sequential pacer of FIG. 8.

DETAILED DESCRIPTION

Figures 1, 2:
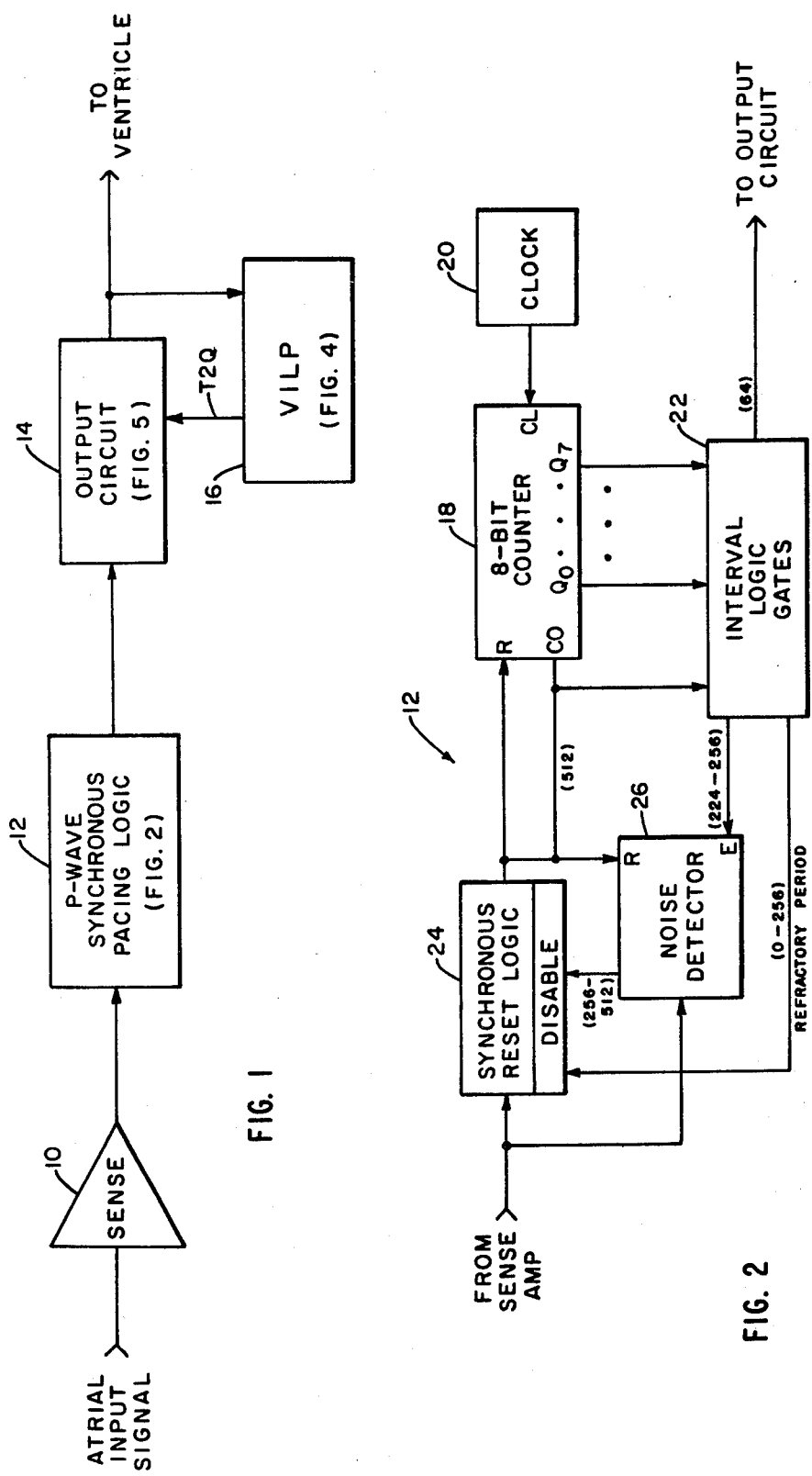
FIG. 1 is a block diagram of the electronic circuitry for an implantable AV synchronous pacer with ventricular-inhibited logic according to the invention.
FIG. 2 is a block diagram of the pacing logic of FIG. 1.

FIG. 1 illustrates the overall functional requirements for an implantable ventricular-inhibited AV synchronous cardiac pacer according to the invention. The electrical components of the pacer are intended to be powered by a lithium compound battery and sealed together with the battery cells in the customary biologically compatible hermetic enclosure, as in the "Omni-Atricor," manufactured by Cordis Corporation, the assignee of the present application. The pacer is implanted at a suitable location in the human body and is electrically interconnected with a two conductor pacer lead which terminates pervenously in a pair of electrodes situated respectively in the right atrium and the bottom of the right ventricle.

In FIG. 1, the atrial lead is connected to the input of an atrial sense amplifier 10 which produces a brief output pulse (e.g., 8 ms) in response to a transition on the atrial lead to a voltage level above a predetermined threshold, which is produced in particular by the P-wave preceding the ventricular contraction. The output of the sense amplifier 10 is applied to a P-wave synchronous pacing logic module 12. Following an AV delay, the pacing logic 12 produces an output pulse which fires an output circuit 14 producing the stimulation pulse output to the ventricular lead. The ventricular lead is also connected to a ventricular-inhibited logic package (VILP) 16 which disables the output circuit following detection of natural or artificial electrical activity on the ventricular lead.

Without the VILP 16, the pacer design of FIG. 1 corresponds generally to the aforementioned Cordis "Omni-Atricor." There are numerous ways of implementing the P-wave synchronous pacing logic 12. The general features of one way are shown in outline form in FIG. 2. The heart of the pacing logic 12 (FIG. 2) is an 8-bit binary counter 18 which counts clock pulses from a clock circuit 20 applied to the clock input of the counter. The counter 18 counts from zero to 511, at which point all 8 bits are binary ones. The 512th pulse from the clock 20 automatically resets the counter and the carry out (CO) output of the counter goes high for one clock cycle. Individual output bits of the counter 18 are tapped for the interval logic gates 22. The interval logic produces various outputs corresponding to the programmed output patterns from the counter 18 which correspond to selected portions of the 512 count cycle. One of the outputs of the logic gates 22 is a binary output line which goes high for one clock cycle at count No. 64, i.e., when only bit position $2^6$ is high. This output goes to the ventricular output circuit which, unless disabled, applies a corresponding stimulation pulse.

The counter 18 has a reset input which, when pulsed by a high logic value, immediately causes the counter 18 to assume the starting position in which all the bits are zero. The reset input is employed to cut short the 512 count cycle. A synchronous reset logic gage 24 receives the pulse output of the atrial sense amplifier 10 and, unless disabled, applies a pulse to the reset input of the counter 18. The reset logic 24 is disabled during an effective refractory period from zero up to count 256 by an output of the interval logic gates 22.

A noise detector 26 which may be of any conventional design also provides a supplementary disable input to the reset logic 24. The detector 26 detects noise which has been picked up by the atrial sense amplifier. By disabling the reset logic, the detector 26 extends the refractory period to the end of the fixed rate cycle (count 512). The noise detector 26 is enabled 32 counts before the end of the refractory period and is reset by the CO output or reset input of the counter 18.

Figure 3:
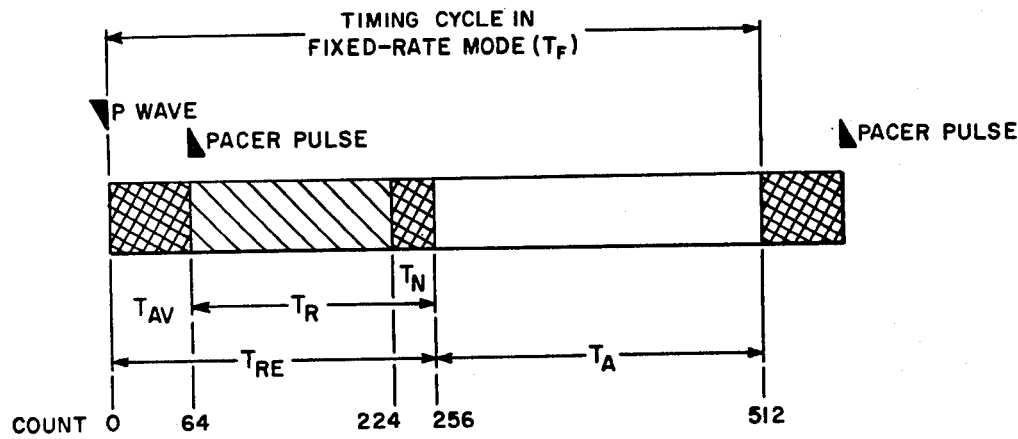
FIG. 3 is a timing diagram for the AV synchronous pacer of FIG. 1.

A timing diagram is shown in FIG. 3 for the pacer of FIGS. 1 and 2. When the counter has counted 64 pulses ($T_{AV}$), the pacer produces a ventricular stimulation output. The effective refractory period ($T_{RE}$) which began with the sensing of the P-wave, continues for another three-eighths of the 512 count cycle or 192 more pulses ($T_R$). If noise is detected during the 32 pulse time window ($T_N$) a latch is set within the noise detector 26 which disables the reset logic 24 for the remainder of the fixed rate cycle, i.e. until count 512 at which time the latch is reset to enable the reset logic. During ($T_{RE}$) the reset logic is disabled so that premature electrical activity cannot reset the counter 18. At the end of the fixed rate period ($T_F$) the counter 18 is automatically set even though there is no P-wave. If the P-wave is sensed in the alert period ($T_A$), the latter half of the cycle, the reset logic, resets the counter to zero thus restarting the next fixed rate period ($T_F$) earlier than scheduled. If the fixed rate pulse is set at 70 beats per minute as determined by programming clock pulse frequency, as the patient's atrial rate increases with exertion, the ventricular stimulation pulses will follow the atrial rate upwards. When the natural atrial rate exceeds 70 beats per minute, the counter 18 is reset early during each cycle. Whenever the patient's atrial rate falls below 70 beats per minute, ventricular stimulation occurs at the fixed rate automatically. Fixed rate operation also occurs whenever noise is detected in a given cycle since the pacer remains refractory to atrial activity over the whole cycle.

Figure 4:
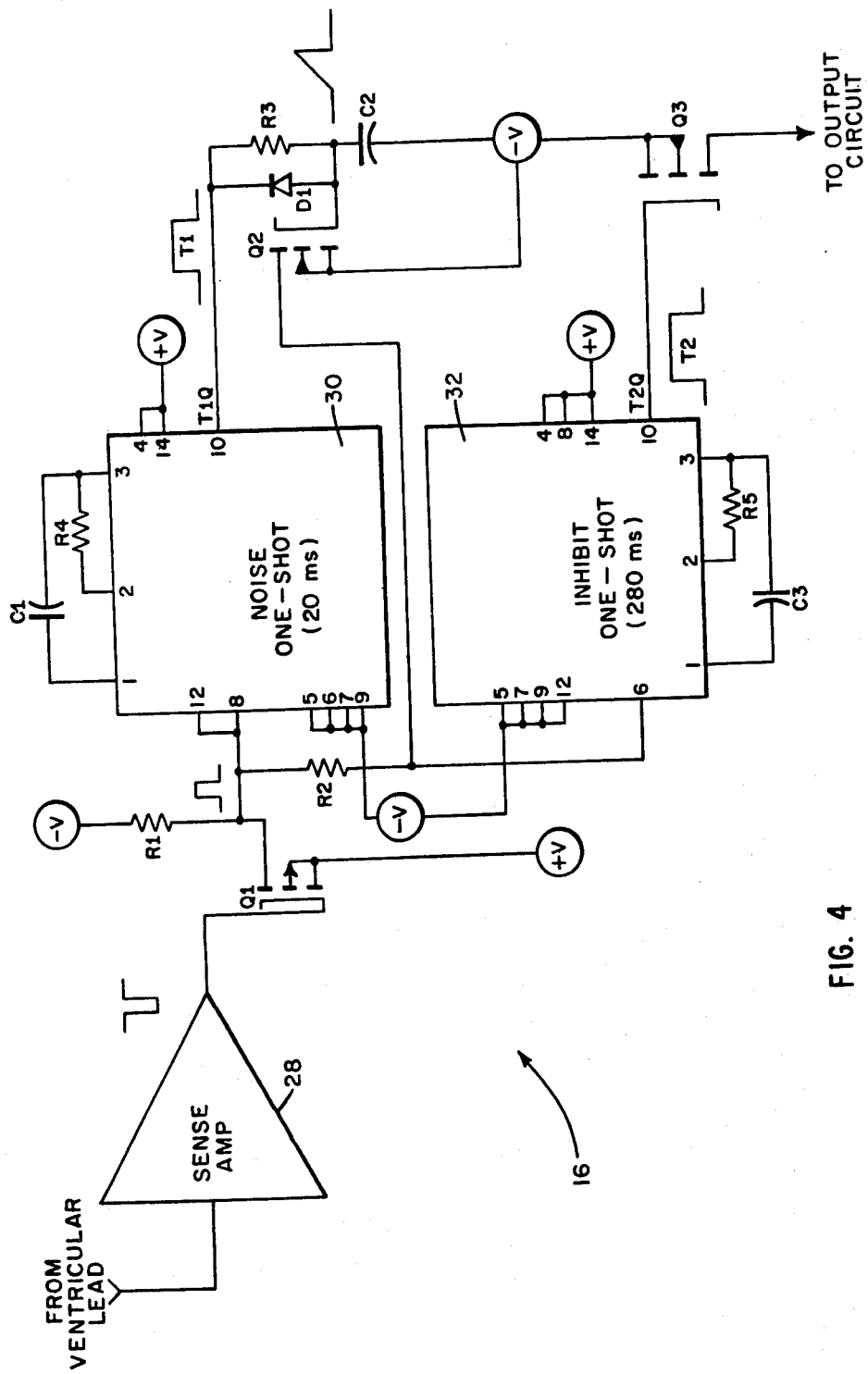
FIG. 4 is a schematic and block diagram of the ventricular-inhibited logic package of FIG. 1.

As shown in FIG. 4, the ventricular-inhibited logic package (VILP) 16 includes its own sense amplifier 28, which is preferably substantially identical to the atrial sense amplifier 10. The amplifier 28 produces a negative-going pulse of about 8 ms duration upon the detection of a voltage transition on the ventricular lead above a predetermined voltage level. The output of the amplifier 28 is applied to the gate of a metal oxide semiconductor field effect transistor (MOSFET) Q1. Transistor Q1 inverts the output of the sense amplifier and applies the resultant upright pulse to the trigger input of a retriggerable noise one-shot 30 (monostable multivibrator) with a nominal astable period (T1) of 20 ms. The one-shot 30 is triggered on the leading edge of the inverted output of the sense amplifier. The output of the inverting circuit Q1 is also applied via resistor R2 to an inhibit one-shot 32 which has a non-retriggerable nominal astable period (T2) of 280 ms. The inhibit one-shot 32 is triggered on the trailing edge of the input pulse so that the pacer output pulse will not be cut short. The lengths of periods T1 and T2 are adjustable by resistors R4 and R5 respectively which in combination with capacitors C1 and C3, respectively, form the RC timing networks for the one-shot circuits.

The output T1Q of retriggerable one-shot 30 is applied to an RC timing network comprising resistor R3 and capacitor C2 which integrates the T1Q output. If there is electromagnetic interference on the ventricular lead at a frequency such that the 20 ms one-shot is retriggered repeatedly, while it is still in the astable state, the output T1Q will stay high for the duration of the detected noise. The T1Q output charges the capacitor C2 toward the supply voltage. The junction between resistor R3 and capacitor C2 is connected to the gate of a common source MOSFET Q2. The drain of the transistor is joined to the trigger input of the inhibit one-shot 32. The input signal to one-shot 32 is thus amplitude modulated by the transistor Q2 to an undetectable level in the presence of noise, while not affecting the input to the noise detector. Diode D1 discharges the capacitor C2 instantaneously when the one-shot 30 fails to be retriggered and returns to the stable state (low).

Figure 5:
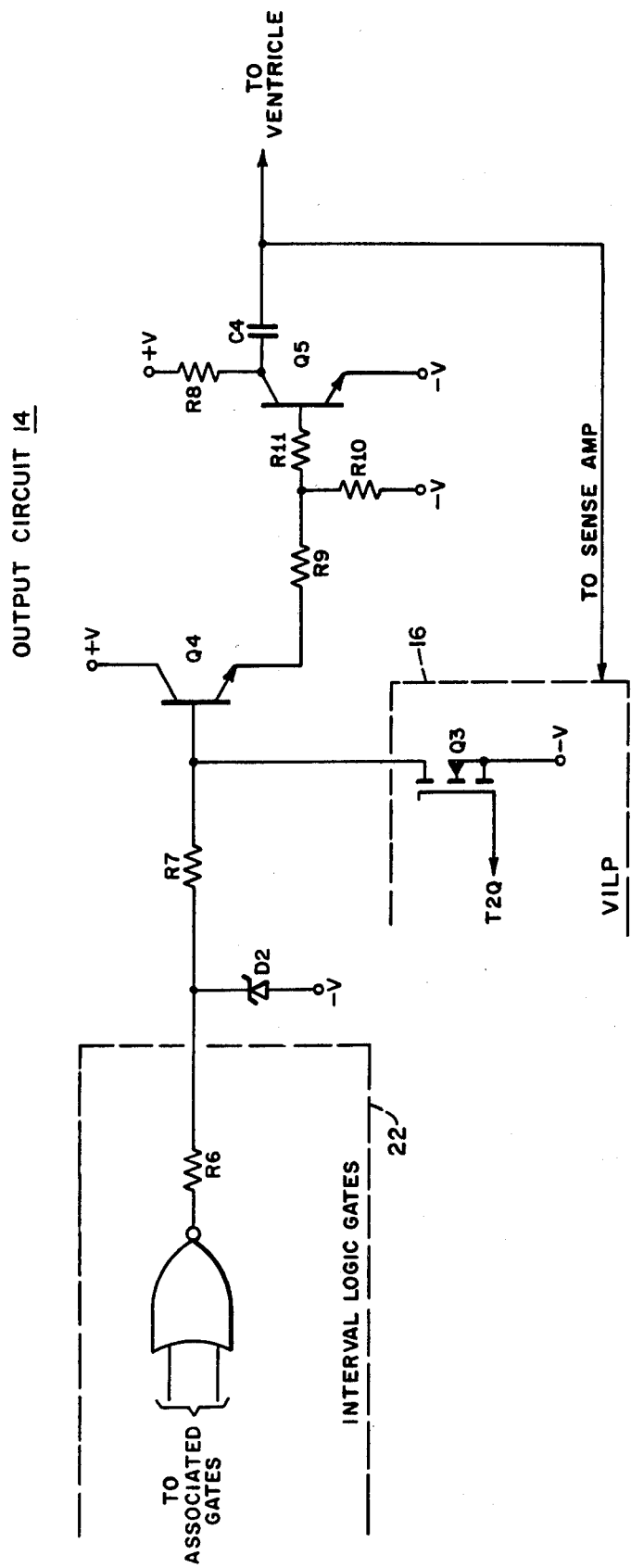
FIG. 5 is a schematic diagram of an embodiment of the output circuit of FIG. 1.

The output T2Q of the 280 ms one-shot 32 is applied to the gate of a pull down MOSFET Q3 which clamps the output circuit to inhibit ventricular stimulation. As shown in FIG. 5 the source of the pull down transistor Q3 is connected to the negative DC voltage supply while the drain is connected to the base of transistor Q4 in the output circuit 14. When the inhibit one-shot is triggered, the output line T2Q goes high for 280 ms. During this interval, transistor Q4 is shorted by clamping the gate to the negative DC voltage supply. This effectively inhibits any stimulation output pulses to the ventricle regardless of the output of the logic gates 22.

Figure 6:
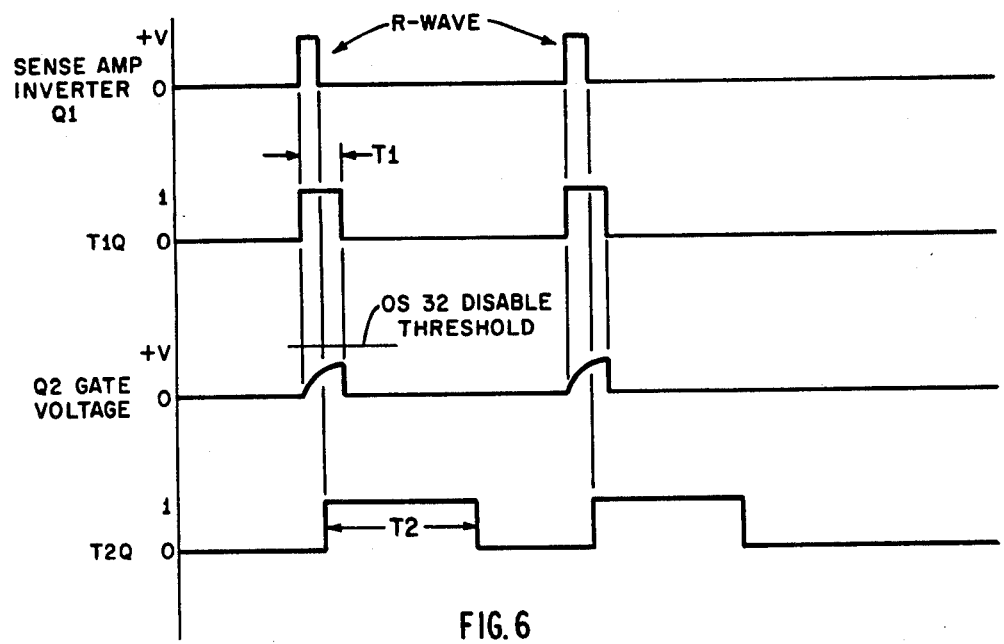
FIG. 6 is a timing diagram of typical waveforms in the ventricular-inhibited logic package of FIG. 4 in normal operation.

As shown in the waveform diagram of FIG. 6, in normal operation, the leading edge of the output of the inverter Q1 of FIG. 4 triggers the 20 ms one-shot. During T1 the charge on capacitor C2 increases the voltage on the gate of Q2. However, 20 ms (T1) is not sufficient time for the capacitor to attain the Q2 gate voltage level at which the trigger input to the 280 ms one-shot is disabled. Meanwhile, the 280 ms one-shot is triggered by the trailing or falling edge of the output of the inverter Q1.

Figure 7:
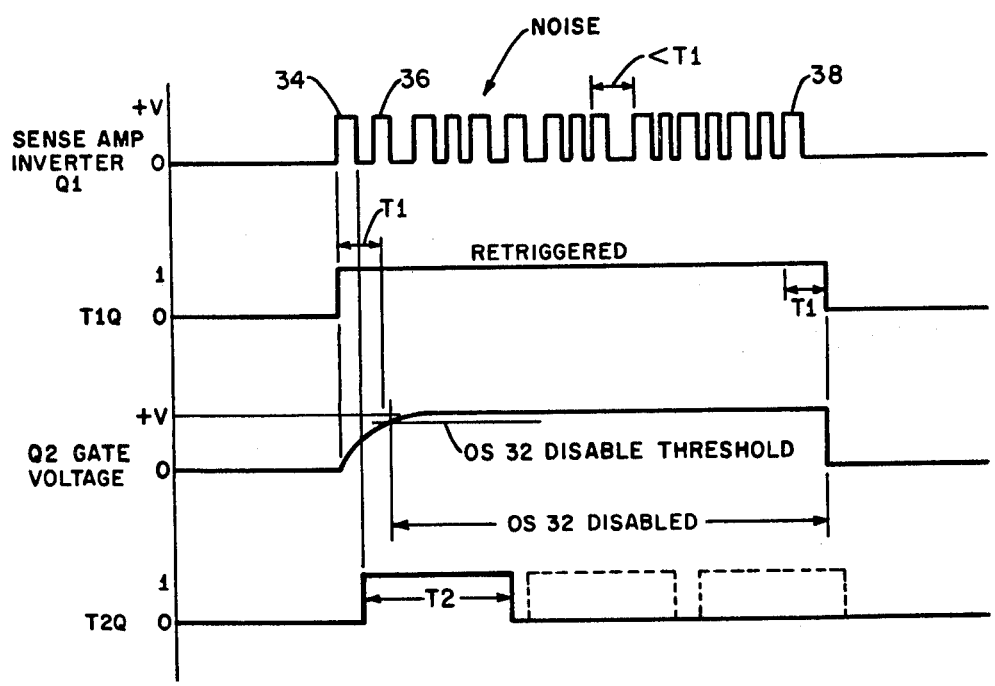
FIG. 7 is a timing diagram of typical waveforms in the ventricular-inhibited logic package of FIG. 4 in the presence of noise.

As shown in FIG. 7, each noise pulse mimics an R-wave and, if permitted to do so, would retrigger the non-retriggerable one-shot 32 every time it returned to the stable state. The VILP circuit is arranged to deny these noise pulses the opportunity to retrigger the inhibit one-shot 32 after the first instance. The first noise pulse 34 triggers the noise one-shot output T1Q on the leading edge and the capacitor C2 begins to charge. The inhibit one-shot is triggered by the trailing edge of pulse 34 and goes into its astable period T2. Meanwhile, before the period T1 has timed out, another noise pulse 36 appears and retriggers the noise one-shot for another period. If each subsequent pulse from Q1 is closely enough spaced to the preceding one, it will retrigger the noise one-shot. The capacitor C2 (Q2 gate) is not discharged but continues to charge to a level where the source-to-drain resistance is so low that the transistor Q2 is effectively a shunt to the negative DC voltage supply. Thus the input to the inhibit one-shot is shorted out. Subsequent noise pulses which occur while T1Q is still high have no effect on T2Q after the interval T1. Following the leading edge of the last noise pulse 38, the retriggerable one-shot output T1Q returns to its stable state and discharges the capacitor C2. Normal operation is thus resumed, and the next pulse is presumed to be a genuine R-wave. The pulses from Q1 in the VILP circuit 16 qualify as R-waves only by virtue of their spacing. Thus stimulation pulses as well as spontaneous natural activity will trigger the one-shots in the VILP circuit.

The ventricular-inhibited AV synchronous pacer of FIG. 1 responds to P-waves during the alert period by resetting the fixed rate timing and issuing a ventricular output pulse after the AV delay. The output pulse is applied to the ventricular lead by the output circuit 14 unless inhibited by the T2Q output of the VILP by detection of an R-wave in the preceding 280 ms.

Electromagnetic interference affects both the atrial and ventricular leads to approximately the same degree because of their proximity. The pacing logic 12 reacts to noise in the time window of its noise detector 26 by going into fixed rate pacing. The need for fixed rate pacing due to noise is determined cycle-by-cycle. Meanwhile, noise on the ventricular lead is picked up by the VILP 16 and after one inhibit period, the VILP is incapacitated. Fixed rate stimulation pulses are issued from the output circuit 14 without being inhibited by the VILP.

In the absence of noise, a spontaneous P-wave followed too closely by an abnormal ventricular beat is handled in the following manner. The P-wave starts the AV delay. Detection of the ectopic ventricular beat by the VILP circuit, during the otherwise refractory AV delay, disables the output of the pacer. Accordingly, at the end of the AV delay, the pulse from the pacing logic has no effect on the output to the ventricle. In the absence of the VILP circuit, injecting a stimulation pulse so soon after an ectopic ventricular beat runs the risk of induced tachycardia, for example, since the stimulation pulse comes during the sensitive Q-T period.

Figure 8:
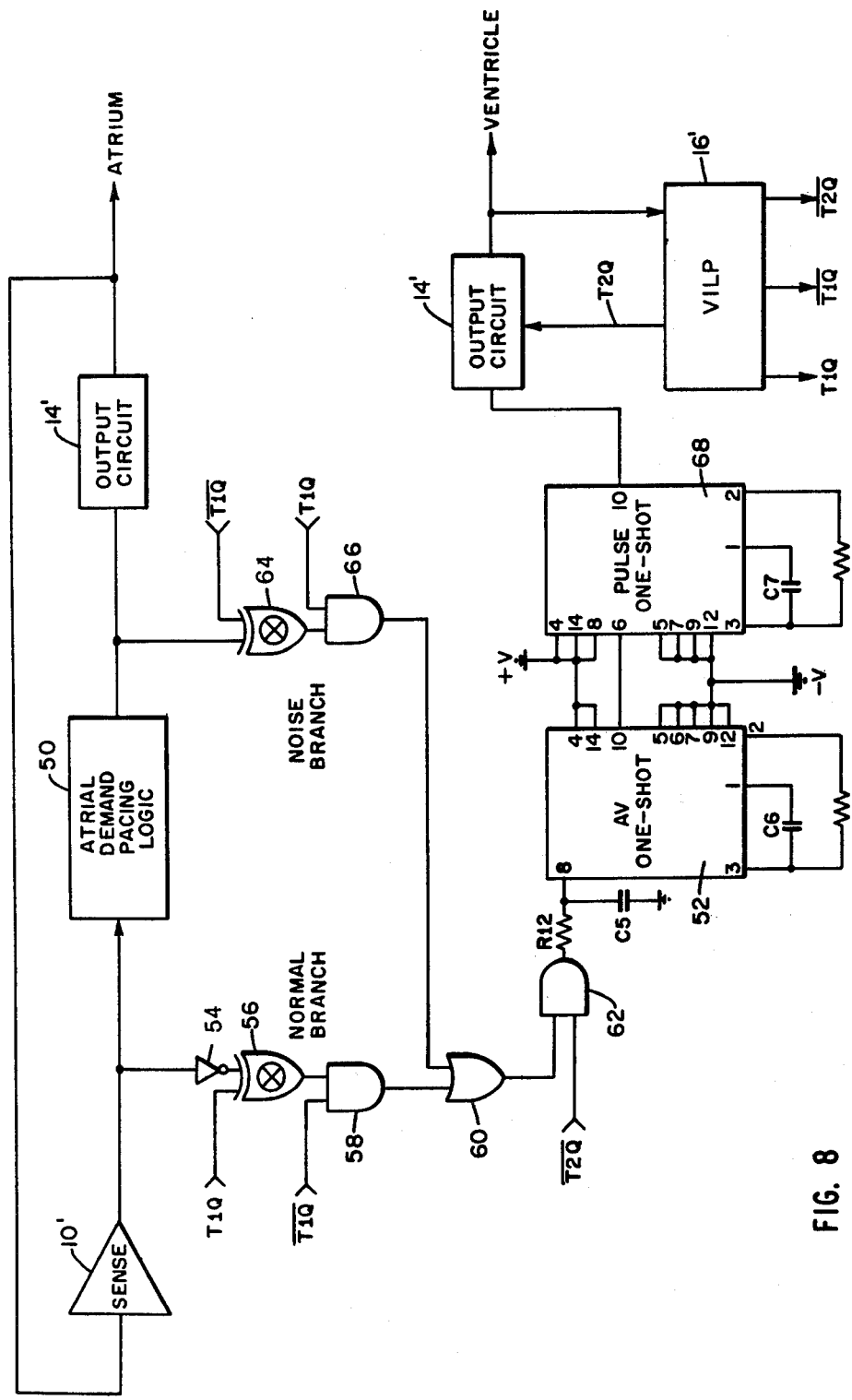
FIG. 8 is a block diagram of an AV sequential pacer incorporating the ventricular-inhibited logic package of FIG. 4.

FIG. 8 illustrates the design of an implantable P-wave synchronized atrial-demand, ventricular-inhibited AV sequential pacer. The object of this pacer is to apply fixed rate atrial pulses to the atrium except when inhibited by the presence of spontaneous sino-atrial action detected by an atrial sense amplifier, and, following an AV delay, to produce ventricular stimulation unless inhibited by the VILP circuit.

The input of atrial sense amplifier 10' is connected to the atrial lead. The output of the amplifier 10' is applied to demand pacing logic 50 which produces output pulses at fixed intervals. The timing interval is restarted by the detection of a genuine P-wave. The output of the atrial pacing logic 50 is applied to an output circuit 14' which is substantially the same as or equivalent to the circuit of FIG. 5. The output circuit 14' applies stimulation pulses to the left atrium via the atrial lead.

Figure 9:
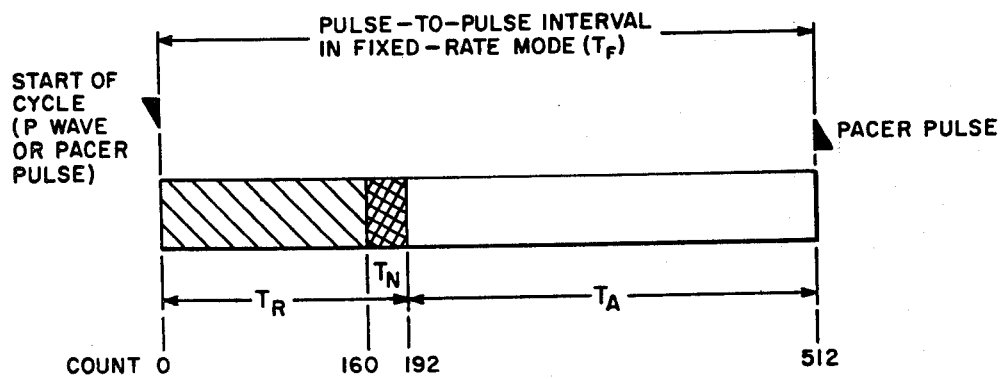
FIG. 9 is a timing diagram for the atrial demand pacing logic of the AV sequential pacer of FIG. 8.

The atrial demand pacing logic 50 corresponds generally to the pacing logic available in the "Omni-Stanicor" manufactured by Cordis Corporation, the assignee of the present application. Functionally, pacing logic 50 is similar to pacing logic 12 shown in FIG. 2. However, the output of the pacing logic 50 which is applied to the output circuit 14' in FIG. 8 does not come at count 64 since there is no AV delay to be timed before applying an output pulse. Instead, the output is supplied directly by the carry out (CO) output of the counter 18 (FIG. 2). CO goes high for one clock cycle on the 512th count. Thus, if the atrial rate is slower than the fixed rate, the counter 18 will produce an output pulse at CO each time it completes the full cycle. The interval timing logic is implemented so that the atrial refractory period ($T_R$) during which the reset logic 24 is disabled, extends from zero up to count 192, as indicated in FIG. 9. The noise sampling interval $T_N$ extends from count 160 to count 192. A P-wave on the atrial lead during the alert period ($T_A$) restarts the 512 count cycle.

In FIG. 8, to trigger the AV delay, the output of the atrial sense amplifier 10' is applied to an AV timing one-shot 52 via a plurality of logic gates 54, 56, 58, 60 and 62 comprising the "normal" branch for the AV trigger signal. An alternate noise branch connects the output of the atrial pacing logic 50 to OR gate 60 via logic gates 64 and 66. Gates 56, 58 and 64, 66 are complementarily operated by the output T1Q and its complement T1Q-bar of the noise one-shot 30 in the VILP circuit 16'. Both of these logic pathways feed into the AV delay one-shot 52. The duration of one-shot 52 is programmed by the RC combination of resistor R13 and capacitor C6. The R12-C5 combination immediately preceding one-shot 52 is used to filter out high frequency switching transients while passing legitimate signals.

A second one-shot 68 detects the falling edge of the AV delay pulse and emits a brief pulse (e.g., 0.9 ms) with a fixed duration determined by R14-C7. The pulse from one-shot 68 proceeds to an output circuit 14'. If allowed by the T2Q output of the VILP circuit, the output circuit applies a corresponding stimulation pulse to the ventricles.

In operation, the AV sequential circuit of FIG. 8 senses an artificial or spontaneous atrial pulse and, in the absence of noise, resets the demand pacing logic. In the normal branch logic, the output of sense amplifier 10' is reinverted and applied to an exclusive OR gate 56 which also receives the output T1Q of the noise one-shot. The output of the exclusive OR gate 56 is applied to AND gate 58 which also receives the complement of the noise one-shot output T1Q-bar. A pulse while T1Q is low, causes AND gate 58 to produce a logic "1" output to AND gate 62 via the OR gate 60. AND gate 62 is gated by the T2Q-bar output of the inhibition one-shot in the VILP circuit 16'. Thus the trigger input to the AV one-shot 52 is inhibited during the ventricular-inhibit period T2Q. That is, if it has been more than 280 ms since the VILP detected ventricular activity, the AV one-shot can be triggered. After the AV delay, one-shot 68 fires the output circuit 14' to apply a ventricular output stimulation pulse to the ventricular lead. If competing ventricular activity has appeared since the triggering of the AV delay, the VILP shorts out the output transistor in the output circuit 14' as in FIG. 5.

Several operational sequences are shown in FIG. 10 for the AV sequential pacer of FIG. 8. These diagrams are intended merely to aid in understanding how the pacer operates, and are not intended as recommendations for use in treating any specific heart disorder. Section A of FIG. 10 illustrates the action of the atrial and ventricular channels when atrial and ventricular stimulation is required. In this case the atrial stimulation pulses appear at the fixed rate since no spontaneous atrial signals are sensed on the atrial lead during the alert period $T_A$. After the fixed AV delay has elapsed without any natural ventricular activity, the pacer issues a ventricular stimulation pulse which initiates a ventricular-inhibited period of approximately 280 ms.

Section B of FIG. 10 illustrates the operation of the atrial and ventricular channels in a hypothetical patient with symptomatic bradycardia but with normal AV conduction. In this case the pacer continues to stimulate the atria at the fixed rate since the patient's natural sinus rate is too slow. However, the fixed AV delay on the ventricular channel is longer than the patient's natural AV conduction period. Consequently, ventricular depolarization occurs spontaneously giving rise to an R-wave which initiates the 280 ms ventricular-inhibited period.

In Section C of FIG. 10 the converse mode is protrayed in which the patient has a normal sinus rhythm but complete heart block characterized by a failure of AV conduction. In this case the sinus rate is faster than the fixed rate. Thus during each alert period $T_A$ a P-wave is sensed and the fixed rate cycle is cut short.

Each time a P-wave is sensed, the AV delay for the ventricular channel is begun. Due to inadequate AV conduction, the AV delay elapses and a ventricular stimulation pulse is issued in each case. This operation simulates that of the AV synchronous pacer.

In Section D of FIG. 10 a completely normal mode of operation is shown in which no stimulation is needed. In this condition the patient's sinus rate is faster than the fixed atrial rate. Via normal AV conduction the somewhat shortened natural AV delay precedes the end of the fixed AV delay thus allowing normal ventricular depolarization. The sensing of the R-wave inhibits ventricular stimulation for 280 ms.

In reference to FIG. 8, if the VILP 16′ detects noise on the ventricular lead the T1Q output stays high until after the noise ends. In this condition the detection of a pulse on the atrial channel fails to produce an output from the exclusive OR gate 56. Since T1Q-bar is low, however, the ensuing high output pulse of the atrial demand pacing logic 50 produces an output from the exclusive OR gate 54 in the noise branch. The output of the exclusive OR gate is gated by the high T1Q noise signal at AND gate 66 through the OR gate 60 to the inhibit gate 62. Gate 62 is enabled since T2Q-bar is high in the noise mode.

When there is noise on the atrial lead, the demand pacing logic 50 automatically shifts to the fixed rate mode. The output of the pacing logic initiates the AV delay via the noise branch since the VILP is also in the noise mode. The end of the AV delay in turn produces fixed rate ventricular stimulation as the output is uninhibited by the VILP. Thus the pacer begins full asynchronous AV sequential operation in the presence of noise.

In the table below, specifications for the circuit components of FIGS. 4, 5 and 8 are offered only by way of illustration of the presently preferred embodiments of the invention. Components of other embodiments may differ substantially.

TABLE

| R1 | 10 megohms | C3 | 0.033 microfarad |
|---|---|---|---|
| R2 | 10 megohms | C4 | 4.77 microfarads |
| R3 | 10 megohms | C5 | 0.1 microfarad |
| R4 | 270 kilohms | C6 | 0.33 microfarad |
| R5 | 2.4 megohms | C7 | 0.1 microfarad |
| R6 | 500 ohms | D1 | 1N914 |
| R7 | 143 kilohms | D2 | Zener 4.3V |
| R8 | 25 kilohms | Q1 | 3N160 |
| R9 | 15 kilohms | Q2 | 3N169 |
| R10 | 100 kilohms | Q3 | 3N169 |
| R11 | 700 ohms | Q4 | 2N930 |
| R12 | 10 kilohms | Q5 | 2N706 |
| R13 | 1.6 megohms | one-shot 30 | CD4047 (RCA CMOS) |
| R14 | 8.2 kilohms | one-shot 32 | CD4047 (RCA CMOS) |
| C1 | 0.033 microfarad | one-shot 52 | CD4047 (RCA CMOS) |
| C2 | 0.033 microfarad | one-shot 68 | CD4047 (RCA CMOS) |

The timing in both the ventricular-inhibited AV synchronous and AV sequential pacer embodiments described above is based on the sino-atrial rate. Thus, the important advantage of physiological pacing is retained, namely, the ability to respond naturally to the body's metabolic needs via the sinus node. In addition, the possibility of competing with spurious ventricular beats is completely eliminated (except in noise) by the VILP, which independently senses genuine ventricular activity and safely shorts out the ventricular output circuit during the sensitive Q-T period. Noise, which might otherwise trick the VILP into inhibiting needed stimulation, is detected by uncomplicated low power timing circuitry.

The VILP provides logic outputs corresponding to the inhibit period (T2Q) and noise (T1Q). In the AV sequential embodiment, these logic outputs switch the AV delay trigger input from the atrial sense amplifier to the safe output of the atrial demand pacing logic in noise. This operation assures that when the ventricular stimulation channel is locked open by noise, the fixed rate atrial stimulation will activate the AV delay rather than noise on the atrial lead. Moreover, the VILP inhibition output (T2Q) gates the AV delay trigger adding another layer of protection. Independently, the pacing logic, in either AV synchronous or AV sequential embodiments, reacts to noise on the atrial lead by converting the output to fixed rate pacing on a cycle-by-cycle basis.

All of the above functions are achieved by adding a small amount of extremely reliable, low power circuitry to existing devices. In the AV synchronous pacer, the only addition is the VILP, which is based on two CMOS one-shots, three MOSFET's, an RC timer and a ventricular sense amplifier which is substantially identical to sense amplifiers long qualified for use in conventional pacers. In the AV sequential pacer, existing pacing logic is employed on the atrial channel. A ventricular output circuit and VILP combination, substantially identical to that for the AV synchronous pacer, is fired by an AV delay and pulse generator comprising a pair of CMOS one-shots. The resulting building-block approach to implementing different pacing modes assures increased reliability through the use of pre-existing circuitry which has been fully qualified for life-supporting cardiac pacers.

Many variations and substitutions may be made in the above circuitry consistent with the fundamental principles of the invention. For example, the RC timing networks used in the VILP and AV delay circuits can be implemented digitally by clock counters and logic gates, if desired. The VILP and AV timing intervals can be externally programmed by additional circuitry, as rate and amplitude are in the Cordis "Omnicor" pacers, for example. See U.S. Pat. No. 3,805,796.

Accordingly, as various changes can be made in the above construction without departing from the scope of the invention, it should be understood that all matter contained in the above description or shown in the accompanying drawings shall be interpreted as illustrative and not in a limiting sense.

What is claimed is:

1. A fully implantable AV sequential pacer including an implantable enclosure with electronic circuitry, wherein the improvement further comprises
    electrical means defining an atrial channel and a ventricular channel,
    means for repeatedly timing a fixed rate interval and for issuing an output pulse at a predetermined point therein,
    means for resetting said timing means to restart the timing of said interval in response to a sensed natural electrical signal on the atrial channel,
    means for stimulating the atria in accordance with said timing means output,
    means responsive to a sensed natural electrical signal on the atrial channel for stimulating the ventricles following a predetermined AV delay in the absence of ventricular activity for a predetermined inhibit period.

2. The pacer of claim 1, the improvement further comprising means responsive to said timing means output for stimulating the ventricles following said AV delay in the presence of electromagnetic interference on said ventricular channel.

3. The pacer of claim 2, the improvement further comprising means for disabling said resetting means in the presence of electromagnetic interference on said atrial channel.

4. A fully implantable cardiac pacer having an implantable enclosure with electronic circuitry, wherein the improvement comprises means defining a first channel associated with one part of the heart and means defining a second channel associated with another part of the heart, means for sensing electrical signals from the heart on said first channel, and for producing a corresponding output, demand pacing logic including first means for repeatedly timing a fixed heart rate interval and issuing an output pulse at a predetermined point in said interval and means for resetting said first timing means in response to the output of said sensing means, whereby the fixed rate interval is restarted, first output circuit means responsive to said first timing means output for applying stimulation pulses on said first channel, delay means responsive to electrical signals on said first channel for producing a delayed logic output following an electrical signal on said first channel, second output circuit means responsive to said delayed output for applying stimulation pulses on said second channel, inhibiting logic means responsive to electrical signals on said second channel for producing an inhibit logic output for a predetermined inhibit interval, shorter than said fixed rate interval, following electrical activity on said second channel, means for disabling said second output circuit means in response to said inhibit output, first noise detection means responsive to electromagnetic interference on said second channel for producing a noise logic output in the presence of noise, and means for disabling said inhibit output in response to said noise logic output.

5. The pacer of claim 4, the improvement further comprising second noise detection means responsive to electromagnetic interference on said first channel for disabling said resetting means in the presence of noise, whereby fixed rate pacing occurs.

6. The pacer of claim 4, the improvement further comprising logic means responsive to said noise logic output for presenting the output of said first sensing means as a trigger input to said delay means in noise-free operation and presenting the output of said pacing logic as a trigger input when noise is present on said second channel.

7. The pacer of claim 6, the improvement further comprising means for gating the trigger input to said delay means with said inhibit output to prevent delay triggering before the end of said inhibit interval.

8. The pacer of claim 4, wherein said inhibiting means includes means for sensing electrical activity on the second channel and for producing a corresponding one-shot trigger pulse, and first one-shot circuit means having a trigger input responsive to said trigger pulse for producing said inhibit logic output.

9. The pacer of claim 8, wherein said noise detection means includes second one-shot circuit means responsive to said trigger pulse for producing a logic output for a noise sampling interval shorter than said predetermined inhibit interval, means for retriggering said second one-shot means while in said sampling interval to continue said logic output for another sampling interval, and means responsive to said second one-shot means for disabling the trigger input to said first one-shot after a predetermined duration of said second one-shot logic output.

10. The pacer of claim 9, wherein said timing means includes a digital counting circuit and said one-shot means are analog one-shot circuits.

11. In a fully implantable single channel demand cardiac pacer having an enclosure with means defining a first channel associated with a part of the heart, a sense amplifier, means for timing a fixed heart rate interval, and means for resetting said timing means in response to noise-free detection of an electrical pulse from the heart on said first channel, and an output circuit responsive to said timing means output for applying stimulation pulses to the heart on said first channel, the improvement comprising circuit means for converting said single channel demand pacer to a dual channel inhibited-output pacer comprising means defining a second channel associated with another part of the heart, delay means triggerable by electrical activity on said first channel for issuing a delayed output, second output circuit means responsive to said delayed output for generating corresponding stimulation pulses to the heart on said second channel, inhibiting logic means responsive to electrical activity on said second channel for producing an inhibit output for an inhibit interval, means for disabling said second output circuit means in response to said inhibit output, noise detection means responsive to electromagnetic interference on said second channel for producing a noise output, and means responsive to said noise output for disabling said inhibit output.

12. The pacer of claim 11, wherein said converting circuit means further includes means for gating the trigger input to said delay means with said inhibit output, whereby the delay is not triggered during the inhibit interval, and switch means responsive to said noise output for switching the trigger input of said delay means from the output of said pacer sense amplifier to the output of said timing means in response to noise on said second channel, whereby fixed rate stimulation pulses on said first channel due to noise on said first channel, result in appropriately delayed stimulation output pulses on said second channel.

13. The pacer of claim 11, wherein said timing means includes a digital counting circuit, said delay means including an analog one-shot circuit.

* * * * *